(12) United States Patent
Ito et al.

(10) Patent No.: US 12,161,652 B2
(45) Date of Patent: Dec. 10, 2024

(54) ANIONIC DRUG-CONTAINING OPHTHALMIC DEVICE

(71) Applicants: SEED CO., LTD., Tokyo (JP); SENJU PHARMACEUTICAL CO., LTD., Osaka (JP)

(72) Inventors: Yuki Ito, Tokyo (JP); Yasuka Watanabe, Tokyo (JP); Sho Koda, Tokyo (JP); Toru Matsunaga, Tokyo (JP); Takao Sato, Tokyo (JP)

(73) Assignees: SEED CO., LTD., Tokyo (JP); SENJU PHARMACEUTICAL CO., LTD., Osaka (JP)

( * ) Notice: Subject to any disclaimer, the term of this patent is extended or adjusted under 35 U.S.C. 154(b) by 932 days.

(21) Appl. No.: 17/256,178

(22) PCT Filed: Jun. 25, 2019

(86) PCT No.: PCT/JP2019/025070
§ 371 (c)(1),
(2) Date: Dec. 25, 2020

(87) PCT Pub. No.: WO2020/004362
PCT Pub. Date: Jan. 2, 2020

(65) Prior Publication Data
US 2021/0268003 A1 Sep. 2, 2021

(30) Foreign Application Priority Data
Jun. 26, 2018 (JP) .................................. 2018-120663

(51) Int. Cl.
| | | |
|---|---|---|
| *A61K 31/352* | (2006.01) | |
| *A61F 2/16* | (2006.01) | |
| *A61F 9/007* | (2006.01) | |
| *A61K 9/00* | (2006.01) | |
| *A61K 31/573* | (2006.01) | |
| *A61L 27/16* | (2006.01) | |
| *A61L 27/52* | (2006.01) | |
| *A61L 27/54* | (2006.01) | |
| *G02C 7/04* | (2006.01) | |

(52) U.S. Cl.
CPC .............. *A61K 31/573* (2013.01); *A61F 2/16* (2013.01); *A61F 9/007* (2013.01); *A61K 9/0051* (2013.01); *A61K 31/352* (2013.01); *A61L 27/16* (2013.01); *A61L 27/52* (2013.01); *A61L 27/54* (2013.01); *G02C 7/04* (2013.01); *A61L 2300/43* (2013.01); *A61L 2430/16* (2013.01)

(58) Field of Classification Search
None
See application file for complete search history.

(56) References Cited

U.S. PATENT DOCUMENTS

| | | |
|---|---|---|
| 9,017,716 B2 | 4/2015 | Satake et al. |
| 2006/0187410 A1 | 8/2006 | Sato et al. |
| 2017/0043017 A1 | 2/2017 | Obata et al. |

FOREIGN PATENT DOCUMENTS

| | | |
|---|---|---|
| DE | 102006004111 | 8/2007 |
| JP | H06-145456 | 5/1994 |
| WO | 2017/145024 | 8/2017 |

OTHER PUBLICATIONS

International Search Report of PCT application PCT/JP2019/025070 filing date: Jun. 26, 2019.
Office Action from JPO Patent Application No. JP2020-505928, Issue date: Jun. 16, 2020.
Decision of refusal from JPO, Patent Application No. JP2020-505928, Issue date: Sep. 1, 2020.
Chinese Office action including English machine translation of Office Action; Patent Application No. 201980041998.0; Date of Drafting: Apr. 18, 2022.
Extended European Search Report of corresponding EP patent application; Patent Application No. EP19824713.2 Date of Drafting: Feb. 8, 2022.
Taiwanese Office action (English machine translation of Office Action) Patent Application No. 108122104 Date of Drafting: Oct. 5, 2022.
EPO Communication of corresponding EP Patent Application No. 19824713.2 Date of Drafting: Jan. 17, 2024.

*Primary Examiner* — Amanda L. Aguirre
(74) *Attorney, Agent, or Firm* — JMB Davis Ben-David

(57) ABSTRACT

The objective of the present invention is to provide a hydrogel having a favorable shape stability not only after releasing an anionic drug contained but also in the process of releasing such an anionic drug, compared with the conventional techniques; and an anionic drug-containing ophthalmic device obtained by applying the hydrogel. The objective can be achieved by an anionic drug-containing ophthalmic device comprising: (1) an anionic drug; and (2) a copolymer which comprises a cationic monomer and a monomer capable of copolymerizing with the cationic monomer, wherein the cationic monomer comprises, as a structural component, a condensation product of (meth) acrylic acid with an aminoalkyl quaternary ammonium compound having a substituted or unsubstituted aralkyl group, or a salt of the condensation product; and the like.

8 Claims, 5 Drawing Sheets

[FIG.1]
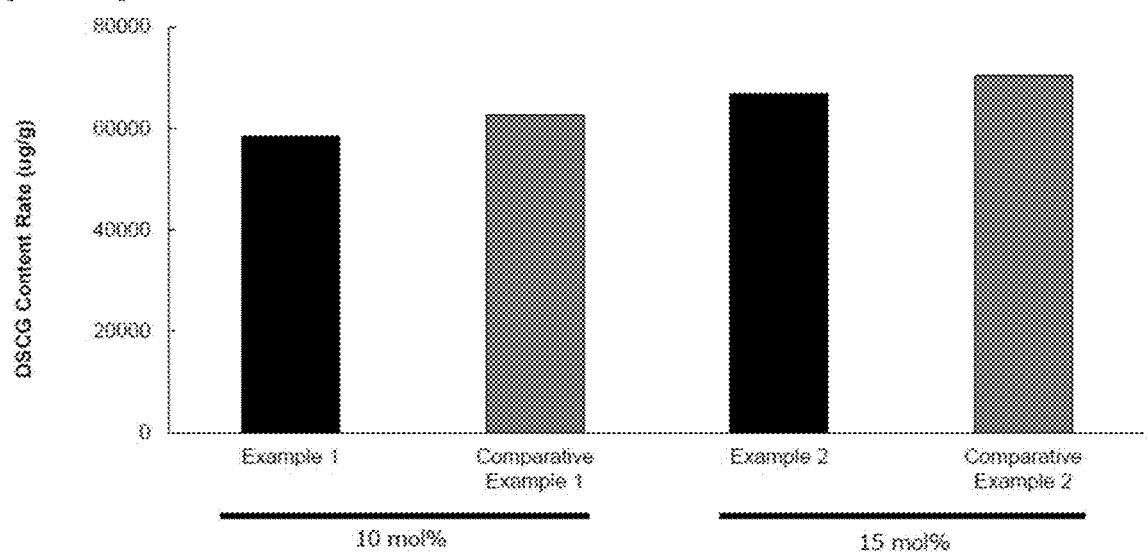

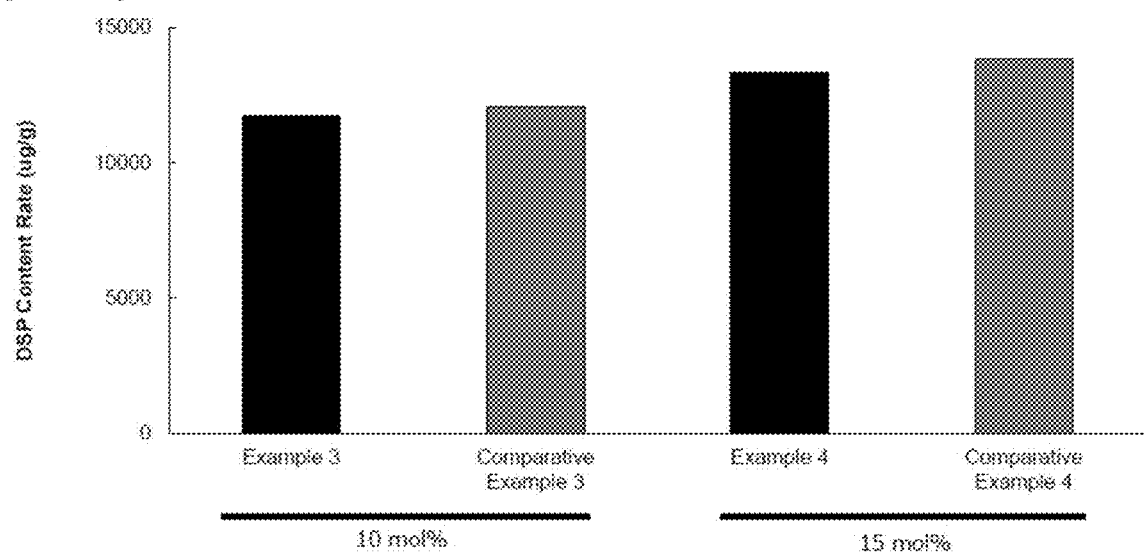
[FIG.2]

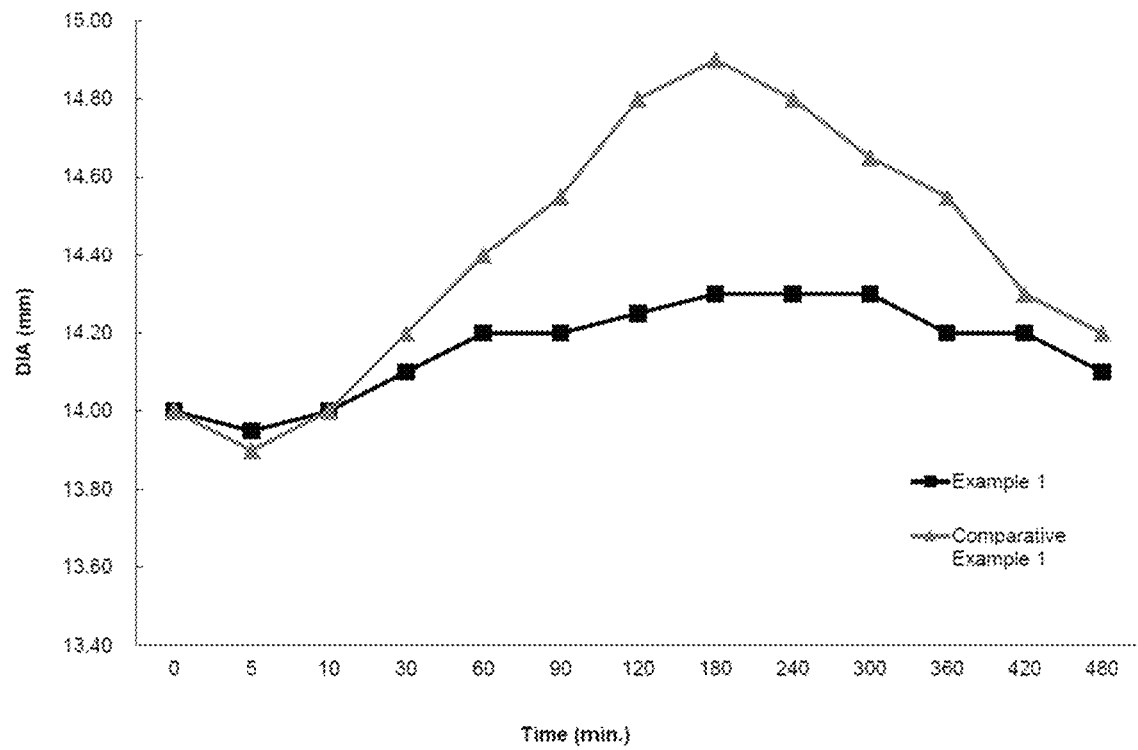
[FIG.3]
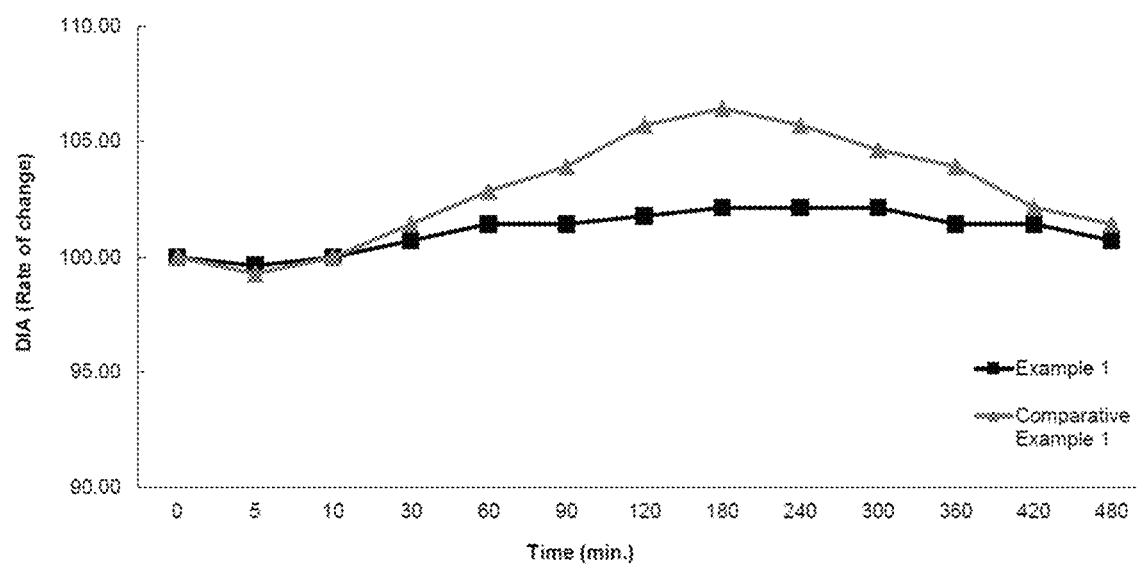
[FIG.4]

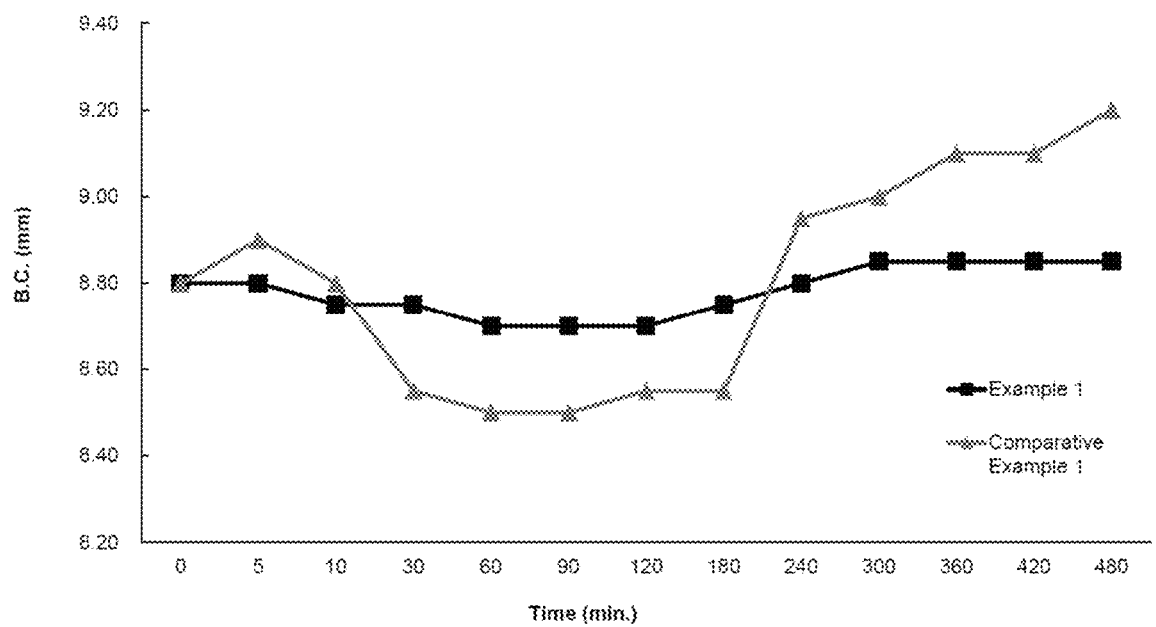

[FIG.6]
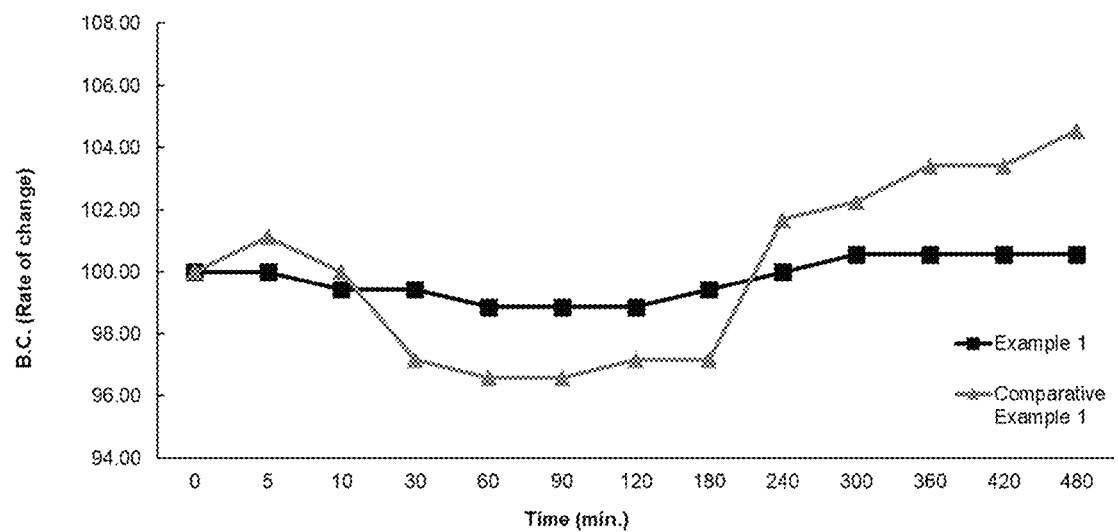

ANIONIC DRUG-CONTAINING OPHTHALMIC DEVICE

TECHNICAL FIELD

The present invention relates to an anionic drug-containing ophthalmic device.

BACKGROUND ART

Methods for intraocular administration for treating ocular disorders as represented by glaucoma, dry eye, pollen allergy include eye drops, eye ointment, internal administration, injection, and the like. Injections directed to treating ocular disorders are invasive treatments that directly treat ocular tissues, such as intravitreal injections. Therefore, injections have a problem of causing pain and foreign body sensation to patients. Furthermore, some intraocular administration methods can give rise to a problem of not achieving the intended effect depending on the dose or method of the drug administration. Therefore, various attempts have been made to find an ocular administration of drug with invasiveness reduced and therapeutic effect exhibited.

For example, when administering a drug by eye drops, the drug in the eye drops is rapidly diluted with tears and discharged by lacrimal passage. Thus, in order to keep the concentration of the drug to an effective level in the eyes, a large dose of drug may be added to the eye drops, or the eye drops may be more frequently administered. When administering a drug by eye ointment, patients with eye ointment administered may go through a temporary poor visibility. The administrations by eye drops and eye ointment consequently give a heavy burden on patients.

In a case wherein a drug is administered to a contact lens wearer by eye drops, the administered drug can entail adverse effects such as shape distortion and/or quality degradation of the contact lens. In this case, an antiseptic that is normally contained in a commercially available ophthalmic drug has a risk for developing allergies to the wearer by incorporating the antiseptic into the contact lens. Therefore, the medicinal therapy with the use of eye drops are not suited to contact lens wearers.

Here, there is a method of drug administration by wearing contact lenses that are made to contain a therapeutic drug in advance for the purpose of treating patients who wear contact lenses in a safe, simple and easy manner. The method of drug administration makes use of a technique that delivers a drug into ocular tissues, i. e., a drug delivery system (DDS).

As a hydrogel applicable as a drug-containing contact lens, known is a hydrogel that adsorbs and holds an anionic drug on a side chain having a quaternary ammonium salt (see Patent Document 1 listed below, which is incorporated by reference herein in its entirety) and a hydrogel in which the molar ratio between an anionic monomer and a cationic monomer, which are structural components, is unbalanced so that an anionic agent can be held in the excess cationic monomer by ionic bonding (see Patent Document 2 listed below, which is incorporated by reference herein in its entirety).

Furthermore, as a cationic monomer being a structural component, known is a hydrogel obtained by using a condensation product or its salt of (meth)acrylic acid with an alkyl quaternary ammonium compound having a substituted or unsubstituted aralkyl group (see Patent Document 3 listed below, which is incorporated by reference herein in its entirety). The use of the hydrogel increases an amount of drug contained and reduces negative effects on gel strength and shape stability after release of the drug.

CITATION LIST

Patent Documents

[Patent Document 1] Japanese Patent Application Laid-Open Publication No. 06-145456
[Patent Document 2] Japanese Patent Application Laid-Open Publication No. 2004-307574
[Patent Document 3] WO 2015/159942

SUMMARY OF THE INVENTION

Problems to be Solved by the Invention

The hydrogels described in Patent Documents 1 to 3 contain a cationic monomer having a cationic group as a structural component of the hydrogel. An anionic agent is bonded to the cationic monomer having such a cationic group by ionic bonding. Therefore, in order to increase the amount of drug contained in the hydrogel, the amount of the cationic monomer contained has to be increased.

However, cationic monomers generally have a very high hydrophilicity. Therefore, an increase in the amount of the cationic monomer contained gives rise to an increase in water content ratio of the resulting hydrogel. The strength of hydrogel decreases depending on the increase in water content ratio. As a result, an increase in the amount of the cationic monomer contained results in not only an increase in the amount of drug contained but also a decrease in the strength of hydrogel depending on the increase in water content ratio. In this case, in order to maintain the mechanical strength of hydrogel, there is a problem that the amount of the cationic monomer added is limited.

Additionally, as a drug-containing hydrogel releases the drug it contains, the shape of the hydrogel can easily become distorted to an undesirable extent. For instance, the hydrogel described in Patent Document 1 keeps showing a desirable shape before it releases the drug because of an interaction between the hydrogel and the drug but, after releasing the drug, the shape of the hydrogel is degraded to an undesirable extent because the interaction becomes no longer existent. The shape degradation after the release of the drug contained is particularly remarkable when the compounding ratio of cationic monomer is high.

The hydrogel described in Patent Document 2 contains an anionic monomer in addition to the cationic monomer as its structural component. The hydrogel as described in Patent Document 2 does not show any remarkable shape degradation after releasing the drug contained because the anionic monomer and the cationic monomer are bonded to each other in it due to an electrostatic interaction between them and the compounding ratio between the anionic monomer and the cationic monomer is not remarkably lopsided. However, when the compounding ratio between the anionic monomer and the cationic monomer is remarkably lopsided in order to increase the amount of drug contained in the hydrogel of Patent Document 2, there arises a risk that the shape of the hydrogel is considerably degraded after the release of the drug contained. As a result, the amounts of anionic monomer and cationic monomer contained are limited. Thus, the hydrogel described in Patent Document 2 is accompanied by a problem that the amount of the drug contained is limited.

On the other hand, the hydrogel base in the ophthalmic device described in Patent Document 3 utilizes, as its structural component, a cationic monomer consisting of a condensation product or its salt of (meth)acrylic acid with an alkyl quaternary ammonium compound having a substituted or unsubstituted aralkyl group. The aralkyl group has a hydrophobic effect due to the benzene ring in the molecule. Even when the amount of cationic monomer contained increases by using such a cationic monomer, both an increase in water content ratio of the hydrogel base and a decrease in strength of the ophthalmic device described in Patent Document 3 due to this are suppressed. As a result, the ophthalmic device described in Patent Document 3 exhibits an excellent shape stability before and after the drug release. Furthermore, the ophthalmic device described in Patent Document 3 can contain a larger amount of drug as compared with the hydrogel described in Patent Document 2.

However, the shape stability of the ophthalmic device described in Patent Document 3 has been evaluated between before releasing the drug and after releasing the drug completely. Therefore, Patent Document 3 does not evaluate the shape stability in the process of releasing the drug.

In general, a shape distortion occurring during wearing of ophthalmic lens such as contact lens and intraocular lens causes eye damages due to a mechanical stimulation and a negative effect on optical characteristics. Such a shape distortion includes a fluctuation in the radius of curvature. In the contact lens, the fluctuation in the radius of curvature changes the refractive index of the lens. Therefore, the fluctuation in the radius of curvature causes a poor visual acuity. In addition, the fluctuation in the radius of curvature causes the adsorption of the lens to the cornea due to the suction cup effect, and eye damages caused by the contact of the central or peripheral portion of the lens with the cornea. Therefore, the shape stability of the ophthalmic lens occurring during wearing should be evaluated not only before and after releasing the drug but also in the process of releasing the drug.

The present inventors prepared the ophthalmic device described in Patent Document 3, and evaluated the shape stability of the ophthalmic device in the process of releasing the anionic drug. As a result, no change in the shape of the ophthalmic device was observed in the comparison before and after releasing the anionic drug. However, it was confirmed that the diameter and radius of curvature of the ophthalmic device were fluctuated in the process of releasing the anionic drug.

Furthermore, there have not been known an ophthalmic device applicable to an ophthalmic lens exhibiting the following characteristics even when the amount of the cationic monomer contained as a structural component increases: suppressing the increase in water content ratio of the ophthalmic device; suppressing the decrease in strength of the base due to the increase in water content ratio; showing a favorable shape stability before and after releasing the anionic drug; and showing a favorable shape stability in the process of releasing the anionic drug.

In view of the above circumstances, problems to be solved by the present invention are to provide a hydrogel having a favorable shape stability not only after releasing an anionic agent contained but also in the process of releasing such an anionic agent as compared with the ophthalmic device described in Patent Document 3; and an anionic drug-containing ophthalmic device obtained by applying the hydrogel.

Means of Solving the Problems

The present inventors made intensive research efforts for the purpose of solving the above identified problems and closely looked into the relationship between the structure of cationic monomer and the water retainability and shape stability of the device base. As a result, the present inventors came to pay attention to a condensation product of (meth) acrylic acid with an alkyl quaternary ammonium compound having aralkyl group and amino group.

Finally, the present inventors have successfully invented an anionic drug-containing ophthalmic device according to the following method: preparing a hydrogel by using as a cationic monomer a condensation in which (meth)acrylic acid is amide-condensed with quaternary ammonium compound having aralkyl group and amino group; and preparing an anionic drug-containing ophthalmic device by incorporating an anionic drug into the hydrogel. Then, the present inventors have found that the resulting ophthalmic device exhibited the following characteristics: suppressing the increase in water content ratio; suppressing the shape change of the ophthalmic device in the process of releasing an anionic drug, which is a problem found out in the ophthalmic device described in Patent Document 3; and showing a favorable shape stability in the process of releasing an anionic drug and in the end of releasing an anionic drug. Such as, the present invention has been completed on the basis of the findings and successful examples that were found or obtained by the present inventors.

Thus, according to the present invention, there is provided an anionic drug-containing ophthalmic device containing (1) an anionic drug; and (2) a copolymer which contains a cationic monomer and a monomer capable of copolymerizing with the cationic monomer, wherein the cationic monomer contains, as a structural component, a condensation product of (meth)acrylic acid with an aminoalkyl quaternary ammonium compound having a substituted or unsubstituted aralkyl group, or a salt of the condensation product.

According to the present invention, preferably the condensation product of (meth)acrylic acid with an aminoalkyl quaternary ammonium compound having a substituted or unsubstituted aralkyl group is expressed by general formula (I) shown below:

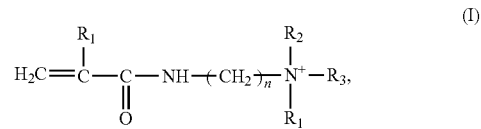

(wherein
R$_1$ represents a hydrogen atom or CH$_3$,
One or each of two or three of R$_2$ through R$_4$ independently represents a functional group expressed by general formula (II) shown below:

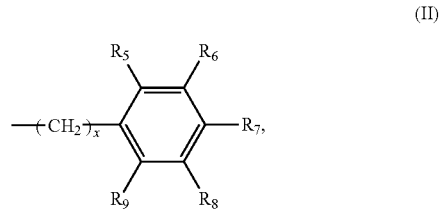

(wherein x represents an integer between 1 and 3 and each of $R_5$ through $R_9$ independently represents a hydrogen atom or a straight or branched chain hydrocarbon group having $C_1$ through $C_6$), each of two, one or nil of the remaining of $R_2$ through $R_4$ represents a straight or branched chain hydrocarbon group having $C_1$ through $C_3$ and n represents an integer between 1 and 4.

According to the present invention, preferably the copolymer of (2) as defined above further contains a hydrophilic monomer as a structural component, and the anionic drug-containing ophthalmic device as defined above is a hydrogel.

According to the present invention, preferably the copolymer of (2) as defined above contains no anionic monomer as a structural component.

According to the present invention, preferably the compounding ratio of the cationic monomer as defined above is between 0.5 mol % and 20 mol % relative to 1 mol of the hydrophilic monomer.

According to the present invention, preferably the anionic drug as defined above is either dexamethasone sodium phosphate or sodium cromoglicate.

Effect of the Invention

The anionic drug-containing ophthalmic device according to one embodiment of the present invention can suppress an increase in water content ratio of the ophthalmic device, suppress a shape change of the ophthalmic device not only in the end of releasing the anionic drug contained but also in the process of releasing the anionic drug contained, and show a favorable shape stability, even when the device contains a highly compounding ratio of the cationic monomer and encompasses a high concentration of the anionic drug.

Therefore, it is expected that, by applying the anionic drug-containing ophthalmic device according to one embodiment of the present invention, an eye disease treatment can be performed effectively; and the foreign-body sensation to wearers of the ophthalmic device and the adverse effects that can be exerted to the optical properties of the ophthalmic device can be suppressed. Furthermore, it is expected that since the ophthalmic device according to one embodiment of the present invention may contain no anionic monomer as a structural component of base copolymer of the ophthalmic device, all the cationic groups in the copolymer can bind to the anionic drug contained.

BRIEF DESCRIPTION OF THE DRAWINGS

FIG. 1 is a graph illustrating the content rate of anionic drug of each of Examples 1 through 2 and Comparative Examples 1 through 2, as described in Examples below.

FIG. 2 is a graph illustrating the content rate of anionic drug of each of Examples 3 through 4 and Comparative Examples 3 through 4, as described in Examples below.

FIG. 3 is a graph illustrating the measured value of the diameter over time of each of Example 1 and Comparative Example 1, as described in Examples below.

FIG. 4 is a graph illustrating the rate of the change in diameter over time of each of Example 1 and Comparative Example 1, as described in Examples below.

FIG. 5 is a graph illustrating the measured value of the radius of curvature over time of each of Example 1 and Comparative Example 1, as described in Examples below.

FIG. 6 is a graph illustrating the rate of the change in radius of curvature over time of each of Example 1 and Comparative Example 1, as described in Examples below.

DESCRIPTION OF EMBODIMENTS

While an ophthalmic device that form one embodiment of the present invention will now be described in detail, the scope of the present invention is not limited only by the following description, and the present invention may take various embodiments to the extent that its objective can be achieved.

An ophthalmic device according to one embodiment of the present invention relates to an anionic drug-containing ophthalmic device capable of being worn into the eye, which can contain and release the anionic drug. The ophthalmic device according to one embodiment of the present invention contains at least (1) an anionic drug and (2) a copolymer. The copolymer of (2) contains as structural components at least a cationic monomer containing a condensation product of (meth)acrylic acid with an aminoalkyl quaternary ammonium compound having a substituted or unsubstituted aralkyl group or a salt of the condensation product, and a monomer capable of copolymerizing with the cationic monomer.

The ophthalmic device according to one embodiment of the present invention is characterized by functioning as a carrier of an anionic drug, and containing a base material of the ophthalmic device that is, as a structural component of copolymer, a cationic monomer containing a condensation product of (meth)acrylic acid with an aminoalkyl quaternary ammonium compound having a substituted or unsubstituted aralkyl group and amino group.

The condensation product of (meth)acrylic acid with an aminoalkyl quaternary ammonium compound having a substituted or unsubstituted aralkyl group and amino group (hereinafter simply referred to as "condensation product") is hydrophilic. The hydrophobic action of the benzene ring in the molecule of the condensation product suppresses a significant increase in water content ratio of the copolymer even when the condensation product is contained in the copolymer at a high ratio. While the scope of the present invention is not bound by any theory or speculation, the ophthalmic device according to one embodiment of the present invention can achieve to increase the amount of drug contained in the ophthalmic device and to suppress an increase in water content ratio of the ophthalmic device by containing the cationic monomer at a high ratio as a structural component of copolymer. As a result, the ophthalmic device according to one embodiment of the present invention can suppress any undesirable fall of strength of the ophthalmic device itself and a high concentration release of the anionic drug contained in the ophthalmic device at the initial stage. Furthermore, even if the ophthalmic device according to one embodiment of the present invention contains as a cationic monomer the condensation product at a high ratio, the shape stability of the ophthalmic device can be maintained due to the actions caused by the benzene ring and the amide bond in the molecule of the condensation product. As such, the ophthalmic device according to one embodiment of the present invention suppresses a change in shape and exhibits a favorable shape stability even in the process of releasing the drug contained at a high concentration.

The cationic monomer used in the ophthalmic device according to one embodiment of the present invention contains at least a condensation product of (meth)acrylic acid with an aminoalkyl quaternary ammonium compound having a substituted or unsubstituted aralkyl group and amino group, or a salt of the condensation product. The condensation product is not particularly limited as long as the condensation product is formed to have a structure of amide condensation in appearance between the carboxyl group of (meth) acrylic acid and the aminoalkyl group of quaternary ammonium compound having a substituted or unsubstituted aralkyl group and amino group, which are constituent units.

The method of manufacturing the condensation product is particularly limited as long as the method includes subjecting (meth)acrylic acid and aminoalkyl quaternary ammonium compound having a substituted or unsubstituted aralkyl group to an amide condensation. The specific examples of the condensation product and the salt include 3-(methacrylamide) propyldimethylbenzylammonium chloride (MAPBAC). MAPBAC is available, for example, from MRC UNITEC.

The cationic monomer may be a mixture of the condensation product or the salt and a monomer having another cationic group.

In a specific mode, for example, the condensation product may be a compound having a structure expressed by general formula (I) shown below:

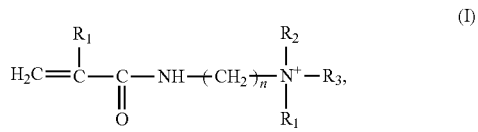

(wherein
$R_1$ represents a hydrogen atom or $CH_3$,
One or each of two or three of $R_2$ through $R_4$ independently represents a functional group expressed by general formula (II) shown below:

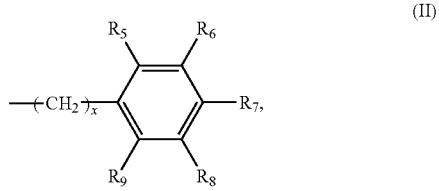

(wherein x represents an integer between 1 and 3 and each of $R_5$ through $R_9$ independently represents a hydrogen atom or a straight or branched chain hydrocarbon group having $C_1$ through $C_6$),
each of two, one or nil of the remaining of $R_2$ through $R_4$ represents a straight or branched chain hydrocarbon group having $C_1$ through $C_3$ and
n represents an integer between 1 and 4.

Among the compounds that are expressed by the general formula (I), those that can suitably be used for the purpose of the present invention are, for example, such ones wherein $R_1$ is a hydrogen atom or $CH_3$ and one of $R_2$ through $R_4$ is a benzyl group, while each of the remaining two is $CH_3$ or $C_2H_5$ and n is an integer that is 1 to 3. Among the compounds that are expressed by the general formula (I), one that can suitably be used for the purpose of the present invention is 3-((meth) acrylamide) propyldimethylbenzylammonium chloride.

The amount of the cationic monomer contained is not subjected to any particular limitations so long as the device can maintain the given shape. For example, the amount of the cationic monomer contained may be between several mol % and tens of several mol % relative to the amount of the hydrophilic monomer contained, which is the second polymerization component as will be described hereinafter. As a specific example of the amount of the cationic monomer contained, it is, relative to a mol of the hydrophilic monomer, preferably within a range not exceeding 30 mol %, more preferably within a range between 0.5 mol % and 20 mol % (between 0.005 mols and 0.2 mols), more preferably within a range between 0.5 mol % and 10 mol % (between 0.005 mols and 0.1 mols). When the amount of the cationic monomer contained is less than 0.5 mol % relative to a mol of the hydrophilic monomer, the quantity of the anionic drug to be contained in the ophthalmic device is reduced. Then, it may be difficult to form an anionic drug-containing ophthalmic device that can provide a satisfactory therapeutic effect. When, on the other hand, the amount of the cationic monomer contained exceeds 30 mol % relative to a mol of the hydrophilic monomer, the resulting ophthalmic device has a reduced flexibility and, furthermore, the ophthalmic device cannot maintain a satisfactory level of strength. Then, the resulting ophthalmic device may provide an uncomfortable wearing sensation to wearer when it is actually worn by the wearer.

The ophthalmic device according to one embodiment of the present invention can be a hydrogel when a hydrophilic monomer is compounded as the second polymerization component in addition to the cationic monomer. The hydrophilic monomer to be used for the purpose of the present invention is not subjected to any particular limitations, as long as it has at least a hydrophilic group and a (meth) acryloyl group or a vinyl group in the molecule and can feasibly be used for polymerization. Examples of hydrophilic monomers that can be used for the purpose of the present invention include hydroxymethyl (meth)acrylate, 2-hydroxyethyl (meth)acrylate, 2-hydroxypropyl (meth)acrylate, 2,3-dihydroxypropyl (meth)acrylate, 2-polyethyleneglycol mono(meth)acrylate, 2-polypropyleneglycol (meth)acrylate, N,N-dimethyl (meth)acrylamide, N,N-diethyl (meth)acrylamide and N-vinyl pyrrolidone. For the purpose of the present invention, the hydrophilic monomer may be used either individually or in combination of two or more of such hydrophilic monomers.

The amount of the hydrophilic monomer contained is not subjected to any particular limitations, as long as the copolymer produced by copolymerization with the hydrophilic monomer can take the form of hydrogel. For example, the amount is, relative to the total weight of all the polymerization components, typically between 50 wt % and 90 wt %, preferably between 60 wt % and 80 wt %. When the amount of the hydrophilic monomer contained is less than 50 wt %, the softness of the obtained ophthalmic device may be low to consequently give an uncomfortable wearing sensation. When, on the other hand, the amount of the hydrophilic monomer contained exceeds 90 wt %, the cationic monomer may not be contained by a sufficient amount.

A hydrophobic monomer may be contained in an anionic drug-containing ophthalmic device according to one embodiment of the present invention as a polymerization component. The hydrophobic monomer can control the outflow rate of the anionic drug into the tear in the eye of the device wearer. Any hydrophobic monomer may be used for the purpose of the present invention provided that it has a poor dissolubility in water, and has one or more (meth)

acryloyl group or a vinyl group in the molecule and can feasibly be used for polymerization. Examples of hydrophobic monomers that can be used for the purpose of the present invention include (meth)acryl-based monomers such as trifluoroethyl methacrylate, methacryl amide, methyl methacrylate, n-butyl methacrylate, tert-butyl methacrylate, benzyl methacrylate, ethylhexyl methacrylate and lauryl (meth)acrylate; silicone-containing monomers such as syloxanyl methacrylate, α-mono(methacryloyloxymethyl)polydimethyl siloxane, α,ω-di(methacryloxymethyl)polydimethyl siloxane, α-mono(3-methacryloyloxypropyl)polydimethyl siloxane, α,ω-di(3-methacryloyloxypropyl)polydimethyl siloxane, α-mono(3-methacryloyloxybutyl)polydimethyl siloxane, α,ω-di(3-methacryloyloxybutyl)polydimethyl siloxane, α-monovinylpolydimethyl siloxane, α,ω-divinylpolydimethyl siloxane, 3-tris(trimethylsiloxy)silylmethyl (meth)acrylate, 3-tris(trimethylsiloxy)silylpropyl (meth)acrylate, 3-methylbis(trimethylsiloxy)silylmethyl (meth)acrylate, 3-methylbis(trimethylsiloxy)silylpropyl (meth)acrylate, 3-trimethylsiloxydimethylsilylmethyl (meth)acrylate, 3-trimethylsiloxydimethylsilylpropyl (meth)acrylate and 3-methyldimethoxysilylpropyl (meth)acrylate. For the purpose of the present invention, any one of such hydrophobic monomers may be used alone or two or more of such hydrophobic monomers may be used in combination.

While the amount of the hydrophobic monomer contained is not subjected to any particular limitations, it is, for example, between 0 wt % and 30 wt %, preferably between 0 wt % and 20 wt %, relative to the total weight of all the polarization components. When the amount of the hydrophobic monomer contained exceeds 30 wt %, the softness of the obtained ophthalmic device may be low to consequently give an uncomfortable wearing sensation.

A cross-linking monomer may be compounded in addition to the above described components of the ophthalmic device according to one embodiment of the present invention. The cross-linking monomer can form a mesh structure in the hydrogel and adjust the mechanical strength of the hydrogel. There are no particular limitations to the cross-linking monomer to be used for this purpose so long as it is a compound having two or more (meth)acryl groups or vinyl groups in the molecule. Examples of cross-linking monomers that can be used for the purpose of the present invention include ethyleneglycol di(meth)acrylate, methylene bis(meth)acrylamide, 2-hydroxy-1,3-di(meth)acryloxypropane and trimethylolpropane tri(meth)acrylate. Any one of such cross-linking monomers may be used alone or two or more of such cross-linking monomers may be combined for use.

While the amount of the cross-linking monomer contained is not subjected to any particular limitations, it is, for example, between 0.3 mol % and 10 mol %, preferably between 0.7 mol % and 3 mol %, relative to the total number of moles of all the polymerization components. When the amount of the cross-linking monomer contained exceeds 10 mol %, the softness of the obtained anionic drug-containing ophthalmic device may be low to consequently give an uncomfortable wearing sensation.

The copolymer in the ophthalmic device according to one embodiment of the present invention can be obtained by subjecting monomer components such as a cationic monomer, a hydrophilic monomer, a hydrophobic monomer and a cross-linking monomer to a copolymerization reaction. In the ophthalmic device according to one embodiment of the present invention, the anionic agent can be held in the inside and on the surface of the ophthalmic device by binding the cationic monomer to the anionic agent by ionic bonding. When an anionic monomer having an anionic group in the side chain is contained as a monomer component of the copolymer, the ionic bonding may be inhibited. Therefore, it is preferable that the copolymer in the ophthalmic device according to one embodiment of the present invention does not contain as a monomer component an anionic monomer selected from the group consisting of (meth)acrylic acid, (meth) acryloyloxyethyl succinic acid, (meth) acryloyloxyethyl phosphate, (meth) acryloyloxymethyl phosphate and (meth) acryloyloxypropyl phosphate. Alternatively, even if the copolymer contains any anionic monomer, the copolymer preferably contains the anionic monomer at the amount in an extent that does not affect the solution of the problems of the present invention.

The ophthalmic device according to one embodiment of the present invention can be manufactured by combining a number of manufacturing steps that are known to those who are skilled in the art. While the method of manufacturing the ophthalmic device according to one embodiment of the present invention is not subjected to any particular limitations, it typically include the following steps: agitating and dissolving a solution prepared by adding a polymerization initiator to a mixture of monomer components constituting a copolymer being a base material of an anionic drug-containing ophthalmic device to obtain a monomer mixture solution; putting the obtained monomer mixture solution into a mold of a desired shape and subjecting the mold to a copolymerization reaction to obtain a copolymer; cooling the mold and releasing the copolymer from the mold, and, if necessary, cutting and/or polishing the copolymer, and subsequently subjecting the copolymer to hydration swelling to obtain a hydrogel; and immersing the obtained hydrogel in a solution containing a dissolved anionic drug to obtain an anionic drug-containing ophthalmic device holding the anionic drug in the inside of the hydrogel.

The method of holding an anionic drug in the inside of hydrogel may include, for example, a method including the following steps:

(1) subjecting a monomer mixture solution obtained by adding a polymerization initiator and an anionic drug to a mixture of monomer components and then by mixing them to a copolymerization reaction followed by swelling the obtained copolymer, and optionally transferring the copolymer into a predetermined solution, wherein the predetermined solution may be a solution containing an anionic drug or a solution containing no anionic drug;

(2) carrying out, using the obtained copolymer obtained by the step of obtaining a copolymer described above in an anionic drug-containing solution, both a holding of the anionic drug and a swelling of the copolymer as a single step, and optionally transferring the copolymer into a predetermined solution, wherein the predetermined solution may be a solution containing an anionic drug or a solution containing no anionic drug;

(3) immersing the obtained hydrogel obtained by the step of obtaining a hydrogel described above in an anionic drug-containing solution and holding the anionic drug in the hydrogel followed by transferring the hydrogel into another predetermined solution, wherein the predetermined solution may be a solution containing an anionic drug or a solution containing no anionic drug; or (4) appropriately combining the steps selected from the group consisting of the above steps (1) to (3).

When an anionic agent is dissolved in a monomer mixture solution in advance in the step of obtaining the monomer mixture solution, a copolymer holding the anionic agent in the inside of the molecular can be obtained in the step of obtaining the copolymer. In this case, an anionic drug-containing ophthalmic device in which the anionic drug is held can be obtained by completing the step of obtaining a hydrogel. Furthermore, when a copolymer is immersed in an aqueous solution in which an anionic agent is dissolved in the step of obtaining a hydrogel, the hydration and swelling of the copolymer and the holding of the anionic agent inside can be simultaneously achieved. In this case, as a result, it is possible to omit one working step.

Polymerization initiators that can be used for the purpose of the present invention include popular radical polymerization initiators, which include peroxide-based polymerization initiators such as lauroyl peroxide, cumene hydro peroxide and benzoyl peroxide; and azo-based polymerization initiators such as azo bis dimethylvarelonitrile and azo bis isobutylonitrile. Any one of such polymerization initiators may be employed alone or two or more of them may be combined for use. The amount of polymerization initiator contained is not subjected to any particular limitations so long as it is sufficient for accelerating the copolymerization of the monomers. For example, the amount may be preferably in the range between 10 ppm and 7,000 ppm relative to the total weight of the total polymerization components.

The step of obtaining a copolymer can successfully be executed, for example, by putting the monomer mixture solution in a mold typically made of metal, glass or plastic, and hermetically sealing the mold; subjecting the monomers to a copolymerization reaction in a manner of leaving the sealed mold in a thermostatic bath or the like, raising the temperature stepwise or continuously to between 25° C. and 120° C. and completing the polymerization in the range between 5 hours and 120 hours. Ultraviolet rays, electron rays, gamma rays or the like may be used for the copolymerization reaction. The solution polymerization may be applied by adding water or an organic solvent to the monomer mixture solution.

In the step of obtaining a hydrogel, the hydrogel can be obtained after the end of the copolymerization reaction by cooling the mold to room temperature, releasing the copolymer from the mold and causing the obtained copolymer to be hydrated and swollen, if necessary, after executing a cutting and/or polishing operation. A liquid for causing the copolymer to be hydrated and swollen (copolymer swelling solution) includes water, saline and isotonic buffer solution and so on. The copolymer reaches a swollen state by a swelling treatment in which the copolymer swelling solution containing the copolymer is heated to the range between 60° C. and 100° C. and the copolymer is immersed in the copolymer swelling solution for a predetermined time period. The swelling treatment is preferably executed so as to remove the unpolymerized monomers contained in the copolymer. The addition of the anionic drug to the copolymer swelling solution and mixing of them allow to achieve the hydration and swelling of the copolymer and the holding of the anionic agent inside simultaneously.

The step of obtaining an anionic drug-containing ophthalmic device can be executed by adopting means known to those skilled in the art such as adding an anionic agent to a monomer mixture solution in advance and mixing them; adding an anionic agent to a copolymer swelling solution and mixing them; immersing a hydrogel in a solution in which an anionic drug is dissolved to hold the anionic drug in the inside of the hydrogel.

The means for holding an anionic drug in the inside of copolymer or hydrogel may be used either individually or in appropriate combination of two or more of such means described above. In the step of obtaining an anionic drug-containing ophthalmic device, after a hydrogel is immersed in a solution in which an anionic drug is dissolved to hold the anionic drug inside, the obtained ophthalmic device may be transferred in another liquid such as physiological saline. Furthermore, if an anionic drug-containing ophthalmic device obtained by applying one or more of means for holding an anionic drug in the inside of copolymer or hydrogel is immersed once again in a solution in which the anionic drug is dissolved, it is expected to improve the amount of anionic drug held inside. The anionic drug is held in the hydrogel by ionic bonding with a cationic group deriving from a cationic monomer that is a structural component of the hydrogel.

The hydrogel can be subjected to a sterilization treatment according to known methods. The hydrogel to be subjected to a sterilization treatment may be a hydrogel holding an anionic drug (that is, an ophthalmic device) or a hydrogel before holding an anionic drug. The solution for immersing a hydrogel to be subjected to a sterilization treatment may be a solution in which an anionic drug is dissolved or a solution in which an anionic drug is not dissolved.

The anionic drug is not subjected to any particular limitations so long as it is a drug having an anionic group such as a sulfo group, a carboxyl group and a phosphoric acid group. Preferable examples of drugs having a sulfo group include azulene sodium sulfonate, dexamethasone meta-sulfobenzoate sodium and chondroitin sulfate sodium. Preferable examples of drugs having a carboxyl group include sodium cromoglicate, potassium cromoglicate, bromfenac sodium, diclofenac sodium, valsartan, dexamethasone sodium phosphate, betamethasone sodium phosphate, moxifloxacin, amlexanox, pranoprofen, norfloxacin, ofroxacin, sodium hyaluronate and chondroitin sulfate sodium. Preferable examples of drugs having a phosphoric acid group include dexamethasone sodium phosphate and betamethasone sodium phosphate. For the purpose of the present invention, any one of such anionic drugs may be used alone or two or more of such anionic drugs may be used in combination. Among them, more preferable examples of anionic drug include dexamethasone sodium phosphate and sodium cromoglicate.

The solvent to be used for dissolving an anionic drug includes, for example, water, hydrophilic solvents and a mixture solvent of water and a hydrophilic solvent. The hydrophilic solvent includes, for example, alcohols such as ethanol, methanol, isopropanol and n-butanol, dimethyl sulfoxide and buffer solutions.

The concentration of the anionic drug contained in the solution in which the anionic drug is dissolved is not subjected to any particular limitations. In other words, the concentration can be selected appropriately by considering the solubility of the anionic drug, the lowest effective concentration necessary for expressing the therapeutic effect of the anionic drug, the safe maximum concentration and so on.

The ophthalmic device according to one embodiment of the present invention can find various applications by manipulating the shape. Specific examples of the ophthalmic device include an ophthalmic lens such as contact lens having a given radius of curvature and a given refractive index. Specific examples of the ophthalmic device include an ophthalmic lens having a shape capable of covering the sclera portion. Such a shape of ophthalmic lens allows an anionic drug to be effectively delivered from the sclera surface to the tissue of the posterior segment tissue of eye. More developing examples of the ophthalmic device according to one embodiment of the present invention include medical devices made to show a sheet-like profile, such as a wound dressing and a poultice.

Now, the present invention will be described in greater detail by way of examples. Note, however, that the present invention is by no means limited by those examples and can be realized in various different modes so long as such modes can dissolve the problems to be solved by the present invention.

EXAMPLES

[Preparation of Anionic Drug-Containing Ophthalmic Devices in Examples (1) Through (4)]

In each of these examples, to a mixture containing 2-hydroxyethylmethacrylate (HEMA) and 3-(methacrylamide) propyldimethylbenzylammonium chloride (MAPBAC) having the compounding ratio relative to 1 mol of HEMA being listed in Table 1, ethyleneglycol dimethacrylate (EDMA) and azo bis isobutyronitrile (AIBN) were added respectively by 0.5% (external) and by 2,500 ppm (external) relative to the total weight of the total polymerization monomers and then they were mixed and agitated to obtain a monomer mixture solution.

The obtained monomer mixture solution was poured into a mold for contact lens and the temperature of the mixture solution was raised to the range between 30° C. and 110° C. for 17 hours to cause a copolymerization reaction. After the copolymerization reaction, the mold was cooled to room temperature and the copolymer was released from the mold. Thereafter, the copolymer was immersed sequentially into a 60° C. warm phosphoric acid buffer solution containing ethanol for 1 hour and into a 60° C. phosphoric acid buffer solution also for 1 hour and then immersed into pure water at room temperature for over 2 hours to obtain a hydrated and swollen hydrogel. In each of Examples (1) and (2), the obtained hydrogel was immersed into a 1.0 wt % (% by weight) aqueous solution of sodium cromoglicate (DSCG), and in each of Examples (3) and (4), the obtained hydrogel was immersed into a 0.2 wt % aqueous solution of dexamethasone sodium phosphate (DSP). Thereafter, the hydrogels were steam-sterilized at 121° C. under high pressure for 30 minutes to obtain the stylized devices of Examples (1) through (4).

[Preparation of Anionic Drug-Containing Ophthalmic Devices in Comparative Examples (1) Through (4)]

In each of Comparative Examples (1) through (4), a hydrated and swollen hydrogel was prepared in the same manner as Examples (1) through (4) except that 2-(methacryloyloxy) ethyldimethylbenzyl ammonium chloride (MOEBAC) described in Patent Document 3 was used at the ratio as listed in Table 1 instead of MAPBAC. In each of Comparative Examples (1) and (2), the obtained hydrogel was immersed in a 1.0 wt % aqueous solution of DSCG and, in each of Comparative Examples (3) and (4), the obtained hydrogel was immersed in a 0.2 wt % aqueous solution of DSP. Thereafter, the hydrogels were steam-sterilized at 121° C. under high pressure for 30 minutes to obtain the stylized devices of Comparative Examples (1) through (4).

[Evaluation Method for Anionic Drug-Containing Ophthalmic Devices]

(1) Measurement of Water Content Ratio

After the high-pressure steam sterilization, the stylized device in each of Examples (1) through (4) and Comparative Examples (1) through (4) was taken out from the drug solution and the excess moisture was wiped out. Subsequently, the weight ($W_1$) of the water-containing device was measured. Thereafter, the device was dried by means of a dryer at 60° C. for 24 hours and then the weight ($W_2$) of the dried device was measured. The water content ratio was determined based on the measured weights by using the mathematical formula shown below. The results are shown in Table 1.

water content ratio (wt %)=[($W_1$-$W_2$)/$W_1$]×100

(2) Evaluation of Wearing Sensation to Wearers Who Wore Lenses for 8 Hours

After the high-pressure steam sterilization, the stylized device in each of Examples (1) and (2) and Comparative Examples (1) and (2) was evaluated on foreign-body sensation to wearers when the wearers who are 10 human panelists wore the device for 8 hours. The stylized device when 0 through 2 wearers answered to feel a foreign-body sensation was evaluated as "++", the stylized device when 3 through 5 wearers answered to feel a foreign-body sensation was evaluated as "+", and the stylized device when 6 or more wearers answered to feel a foreign-body sensation was evaluated as "x". The results are shown in Table 1.

(3) Measurement of Anionic Drug Content Rate

After the high-pressure steam sterilization, the stylized device in each of Examples (1) through (4) and Comparative Examples (1) through (4) was immersed in saline at room temperature in order to cause the device to release (gradually release) the anionic drug contained inside into saline. The anionic drug in saline was quantified over time by means of high performance liquid chromatography (HPLC, available from JASCO Corporation) in accordance with a known method. The anionic drug content rate (μg/g) per the device was calculated using the obtained values.

(4) Shape Stability

With respect to the stylized device in each of Examples (1) and (2) and Comparative Examples (1) and (2) after measuring the anionic drug content rate, the diameter (mm) and the radius of curvature (mm) were measured over time using an Optimec Analyzer (is830, available from Optimic Inc.). In addition, according to the following formula using the measured values, the rate of change in the diameter or the radius of curvature of the device was calculated at the time when the anionic drug was gradually released for t minutes. The results of the actually measured value of the diameter are shown in Tables 2 and FIG. 3, and the results of the rate of change in the diameter are shown in Tables 2 and FIG. 4. The results of the actually measured value of the radius of curvature are shown in Tables 3 and FIG. 5, and the results of the rate of change of the radius of curvature are shown in Tables 3 and FIG. 6.

Rate of change (%)=[value at sustained release time (0 minutes)]÷[value at sustained release time (t minutes)]×100

TABLE 1

| Components | Example 1 (10 mol %) Molar ratio | Example 1 wt % | Comparative Example 1 Molar ratio | Comparative Example 1 wt % | Example 2 (15 mol %) Molar ratio | Example 2 wt % | Comparative Example 2 Molar ratio | Comparative Example 2 wt % | Example 3 (10 mol %) Molar ratio | Example 3 wt % | Comparative Example 3 Molar ratio | Comparative Example 3 wt % | Example 4 (15 mol %) Molar ratio | Example 4 wt % | Comparative Example 4 Molar ratio | Comparative Example 4 wt % |
|---|---|---|---|---|---|---|---|---|---|---|---|---|---|---|---|---|
| HEMA | 90 | 79.8 | 90 | 80.5 | 85 | 71.3 | 85 | 72.2 | 90 | 79.8 | 90 | 80.5 | 85 | 71.3 | 85 | 72.2 |
| MAPBAC | 10 | 20.2 | — | — | 15 | 28.7 | — | — | 10 | 20.2 | — | — | 15 | 28.7 | — | — |
| MOEBAC | — | — | 10 | 19.5 | — | — | 15 | 27.8 | — | — | 10 | 19.5 | — | — | 15 | 27.8 |
| Total | 100 | 100 | 100 | 100 | 100 | 100 | 100 | 100 | 100 | 100 | 100 | 100 | 100 | 100 | 100 | 100 |
| ED | — | 0.5 | — | 0.5 | — | 0.5 | — | 0.5 | — | 0.5 | — | 0.5 | — | 0.5 | — | 0.5 |
| AIBN | — | 0.25 | — | 0.25 | — | 0.25 | — | 0.25 | — | 0.25 | — | 0.25 | — | 0.25 | — | 0.25 |
| Anionic drug | DSCG | | DSCG | | DSCG | | DSCG | | DSP | | DSP | | DSP | | DSP | |
| Water content ratio (%) | 37.5 | | 35.8 | | 37.0 | | 35.3 | | 37.3 | | 36.1 | | 37.4 | | 35.1 | |
| Wearing sensation | ++ | | + | | ++ | | + | | − | | − | | − | | − | |

TABLE 2

| | Example 1 | | Comparative Example 1 | |
|---|---|---|---|---|
| Time (min) | Actually measured values of DIA (mm) | Rate of change % | Actually measured values of DIA (mm) | Rate of change (%) |
| 0 | 14.00 | 100.00 | 14.00 | 100.00 |
| 5 | 13.95 | 99.64 | 13.90 | 99.29 |
| 10 | 14.00 | 100.00 | 14.00 | 100.00 |
| 30 | 14.10 | 100.71 | 14.20 | 101.43 |
| 60 | 14.20 | 101.43 | 14.40 | 102.86 |
| 90 | 14.20 | 101.43 | 14.55 | 103.93 |
| 120 | 14.25 | 101.79 | 14.80 | 105.71 |
| 180 | 14.30 | 102.14 | 14.90 | 108.43 |
| 240 | 14.30 | 102.14 | 14.80 | 105.71 |
| 300 | 14.30 | 102.14 | 14.65 | 104.64 |
| 360 | 14.20 | 101.43 | 14.55 | 103.93 |
| 420 | 14.20 | 101.43 | 14.30 | 102.14 |
| 480 | 14.10 | 100.71 | 14.20 | 101.43 |
| Maximum | 14.30 | 102.14 | 14.90 | 106.43 |
| Minimum | 13.95 | 99.64 | 13.90 | 99.29 |

TABLE 3

| | Example 1 BC | | Comparative Example 1 BC | |
|---|---|---|---|---|
| Time (min) | Actually measured values of B.C. (mm) | Rate of change (%) | Actually measured values of B.C. (mm) | Rate of change (%) |
| 0 | 8.80 | 100.00 | 8.80 | 100.00 |
| 5 | 8.80 | 100.00 | 8.90 | 101.14 |
| 10 | 8.75 | 99.43 | 8.80 | 100.00 |
| 30 | 8.75 | 99.43 | 8.55 | 97.16 |
| 60 | 8.70 | 98.86 | 8.50 | 96.59 |
| 90 | 8.70 | 98.86 | 8.50 | 96.59 |
| 120 | 8.70 | 98.86 | 8.55 | 97.16 |
| 180 | 8.75 | 99.43 | 8.55 | 97.16 |
| 240 | 8.80 | 100.00 | 8.95 | 101.70 |
| 300 | 8.85 | 100.57 | 9.00 | 102.27 |
| 360 | 8.85 | 100.57 | 9.10 | 103.41 |
| 420 | 8.85 | 100.57 | 9.10 | 103.41 |
| 480 | 8.85 | 100.57 | 9.20 | 104.55 |
| Maximum | 8.85 | 100.57 | 9.20 | 104.55 |
| Minimum | 8.70 | 98.86 | 8.50 | 96.59 |

What the abbreviations in Tables stand for are described below.
HEMA: 2-hydroxyethyl methacrylate
MOEBAC: methacryloxyethyl dimethylbenzyl ammonium chloride
MAPBAC: 3-(methacrylamide) propyldimethylbenzylammonium chloride
EDMA: ethyleneglycol dimethacrylate
AIBN: azo bis isobutyronitrile
DSCG: sodium cromoglicate
DSP: dexamethasone sodium phosphate
DIA: diameter
B.C.: radius of curvature

[Evaluation Results]

FIG. 1 and FIG. 2 are graphs showing the anionic drug content rate with respect to the ophthalmic devices of Examples (1) through (4) and Comparative Examples (1) through (4), respectively. As shown in FIG. 1, there has been not found any difference between the content rate of DSCG as an anionic drug with respect to Examples (1) through (2) and Comparative Examples (1) through (2) respectively, provided that the molar ratio of cationic monomer is identical. In addition, while Examples (1) and uses MAPBAC that is a condensation product of (meth)acrylic acid with an aminoalkyl quaternary ammonium compound having a substituted or unsubstituted aralkyl group, Comparative Examples (1) and (2) use MOEBAC that is a condensation product of (meth)acrylic acid with an alkyl quaternary ammonium compound having a substituted or unsubstituted aralkyl group and a carboxyl group.

Furthermore, there has also been not found any difference between the content rate of DSP as an anionic drug with respect to Examples (3) through (4) using MAPBAC and Comparative Examples (3) through. (4) using MOEBAC, respectively. It was demonstrated that Examples (1) through (4) had a similar content rate of anionic drug with Comparative Examples (1) through (4).

FIG. 3 and FIG. 4 are graphs showing the results of the actually measured value of the diameter and the rate of change of the diameter over time in the process or releasing the anionic drug with respect to the ophthalmic devices of Example (1) and Comparative Example (1), respectively. As shown in FIG. 3 and FIG. 4, both Example (1) and Comparative Example (1) exhibited almost no change in shape between before (0 minutes) and after (480 minutes) releasing the anionic drug.

However, in the process of releasing the anionic drug, Comparative Example (1) significantly expanded (maximum diameter 14.90 mm; maximum rate of change 106.43%) from 10 minutes to 180 minutes after the release of drug, and then shrank from 180 minutes to 480 minutes after the release of drug. Finally, the shape approached to that at 0 minutes.

On the other hand, as shown in FIG. 3 and FIG. 4, Example (1) expanded between 10 minutes and 180 minutes, and then shrank. However, the degree of change in shape of Example (1) was smaller than that of Comparative Example (1), and there was almost no change in shape with respect to the stylized device.

FIG. 5 and FIG. 6 are graphs showing the results of the actually measured value of the radius of curvature and the rate of change of the radius of curvature over time in the process of releasing the anionic drug with respect to the ophthalmic devices of Example (1) and Comparative Example (1), respectively. It was confirmed in reference to the graphs of FIG. 5 and FIG. 6 that while Example (1) had almost no change in the radius of curvature since 0 minutes regardless of the time of releasing the drug, Comparative Example (1) had a significant change in the radius of curvature in the process of releasing the drug.

In addition, Table 1 shows the evaluation results of wearing sensation to wearers who wore the stylized device for 8 hours. While there were no wearers who answered to feel a foreign-body sensation among those wearing the ophthalmic devices of Examples (1) and (2) using MAPBAC as a cationic monomer, there were wearers who answered to feel a foreign-body sensation among those wearing the ophthalmic devices of Comparative Examples (1) and (2) using MOEBAC as a cationic monomer.

As described above, according to one embodiment of the present invention, by containing as a structural component of copolymer which serves to a carrier of anionic drug a condensation product of (meth)acrylic acid with an aminoalkyl quaternary ammonium compound having a substituted or unsubstituted aralkyl group or a salt of the condensation product to be employed as at least one cationic monomer, constituted can be an anionic drug-ophthalmic device showing a favorable shape stability in the process of releasing the anionic drug.

INDUSTRIAL APPLICABILITY

An ophthalmic device according to one embodiment of the present invention can be made to take in a desired quantity of anionic drug in a controlled manner and shows excellent gel strength and remarkable shape stability both after and in the process of releasing the anionic drug contained so that it is highly safe to the wearer of the device and can provide an excellent therapeutic effect. It can contribute to human health and welfare.

CROSS REFERENCE TO RELATED APPLICATIONS

This is the US National Stage of International Patent Application No. PCT/JP2019/025070, filed Jun. 25, 2019, which claims the benefit of priority of Japanese Patent Application No. 2018-120663, filed on Jun. 26, 2018, which is incorporated by reference herein in its entirety.

The invention claimed is:

1. An anionic drug-containing ophthalmic device comprising:
   (1) an anionic drug; and
   (2) a copolymer which comprises a cationic monomer and a monomer capable of copolymerizing with the cationic monomer, wherein
the cationic monomer comprises 3-((meth) acrylamide) propyldimethylbenzylammonium chloride.

2. The anionic drug-containing ophthalmic device according to claim 1, wherein the anionic drug is either dexamethasone sodium phosphate or sodium cromoglicate.

3. The anionic drug-containing ophthalmic device according to claim 1, wherein the copolymer of (2) further comprises a hydrophilic monomer as a structural component, and the anionic drug-containing ophthalmic device is a hydrogel.

4. The anionic drug-containing ophthalmic device according to claim 3, wherein the compounding ratio of the cationic monomer is in the range between 0.5 mol % and 20 mol % relative to 1 mol of the hydrophilic monomer.

5. The anionic drug-containing ophthalmic device according to claim 4, wherein the anionic drug is either dexamethasone sodium phosphate or sodium cromoglicate.

6. The anionic drug-containing ophthalmic device according to claim 3, wherein the anionic drug is either dexamethasone sodium phosphate or sodium cromoglicate.

7. The anionic drug-containing ophthalmic device according to claim 1, wherein the copolymer of (2) comprises no anionic monomer as a structural component, and the anionic drug-containing ophthalmic device is a hydrogel.

8. The anionic drug-containing ophthalmic device according to claim 7, wherein the anionic drug is either dexamethasone sodium phosphate or sodium cromoglicate.

* * * * *